US010987672B2

(12) United States Patent
Pennie

(10) Patent No.: US 10,987,672 B2
(45) Date of Patent: Apr. 27, 2021

(54) DUAL PISTON CENTRIFUGE TUBE

(71) Applicant: Patrick Pennie, Fort Myers, FL (US)

(72) Inventor: Patrick Pennie, Fort Myers, FL (US)

(73) Assignee: Emcyte Corp., Fort Myers, FL (US)

(*) Notice: Subject to any disclaimer, the term of this patent is extended or adjusted under 35 U.S.C. 154(b) by 326 days.

(21) Appl. No.: 16/004,053

(22) Filed: Jun. 8, 2018

(65) Prior Publication Data

US 2018/0353954 A1    Dec. 13, 2018

Related U.S. Application Data

(60) Provisional application No. 62/516,755, filed on Jun. 8, 2017.

(51) Int. Cl.
*B01L 3/00* (2006.01)
*B04B 5/04* (2006.01)
(Continued)

(52) U.S. Cl.
CPC ....... *B01L 3/50825* (2013.01); *A61M 1/3693* (2013.01); *B01L 3/50215* (2013.01);
(Continued)

(58) Field of Classification Search
CPC ............. B01L 3/50825; B01L 3/50215; B01L 2200/026; B01L 2200/0689; B01L 2300/0832; B01L 2400/0478; B01L 2300/0858; A61M 1/3693; G01N 33/491; B04B 5/0442; B04B 2005/0485
See application file for complete search history.

(56) References Cited

U.S. PATENT DOCUMENTS 6,123,655 A * 9/2000 Fell .................... A61M 1/3693
494/50
6,733,433 B1 * 5/2004 Fell .................... A61M 1/3693
435/2

(Continued)

FOREIGN PATENT DOCUMENTS

GB          2393670 A  *  4/2004

*Primary Examiner* — Charles Cooley
(74) *Attorney, Agent, or Firm* — William E. Noonan

(57) ABSTRACT

A dual piston centrifuge tube includes an elongate tubular receptacle having upper and lower ends interconnected by a sidewall. First and second common inlet/outlet ports are formed respectively in the upper and lower ends of the tubular receptacle. First and second liquid impermeable pistons are mounted within an interior chamber of the tubular receptacle for sliding longitudinally therein. The first piston is interconnected to the first port by a flexible fluid-conducting pipe that extends through the first piston to communicate with a region of the chamber between the first and second pistons. Blood or other biological fluid is introduced through the first port and pipe into the tubular receptacle to drive the first piston upwardly. The tube is centrifuged to separate the fluid into a plurality of constituent component levels between the first and second pistons. One of the layers is aspirated through the pipe and first port and re-introduced into the receptacle through the second port. The tube is centrifuged a second time to separate the re-introduced fluid into constituent components, which are then aspirated through the second port.

19 Claims, 9 Drawing Sheets

(51) Int. Cl.
*A61M 1/36* (2006.01)
*G01N 33/49* (2006.01)

(52) U.S. Cl.
CPC ......... *B04B 5/0442* (2013.01); *G01N 33/491* (2013.01); *B01L 2200/026* (2013.01); *B01L 2200/0689* (2013.01); *B01L 2300/0832* (2013.01); *B01L 2300/0858* (2013.01); *B01L 2400/0478* (2013.01); *B04B 2005/0485* (2013.01)

(56) References Cited

U.S. PATENT DOCUMENTS

| | | | |
|---|---|---|---|
| 7,976,796 B1* | 7/2011 | Smith | B01L 3/5021 222/249 |
| 9,440,243 B2* | 9/2016 | Chapman | G01N 33/491 |
| 9,573,130 B2* | 2/2017 | Hassouneh | B01L 3/5021 |
| 9,610,590 B2* | 4/2017 | Hamandi | A61M 1/3693 |
| 10,183,042 B2* | 1/2019 | Leach | B01L 3/502 |
| 10,576,130 B2* | 3/2020 | Matuska | A61K 38/1833 |
| 10,773,262 B2* | 9/2020 | Camisani | B04B 5/0442 |
| 2004/0251217 A1* | 12/2004 | Leach | B01L 3/5021 210/787 |
| 2005/0109716 A1* | 5/2005 | Leach | B01L 3/502 210/787 |
| 2006/0196885 A1* | 9/2006 | Leach | A61M 11/06 222/82 |
| 2006/0273050 A1* | 12/2006 | Higgins | G01N 33/491 210/787 |
| 2006/0278588 A1* | 12/2006 | Woodell-May | A61K 35/28 210/787 |
| 2009/0221075 A1* | 9/2009 | Dorian | C12M 47/04 435/379 |
| 2010/0140182 A1* | 6/2010 | Chapman | B01D 21/262 210/741 |
| 2011/0284460 A1* | 11/2011 | Leach | B01L 3/50215 210/513 |
| 2015/0367064 A1* | 12/2015 | Pennie | B01L 3/50215 494/37 |
| 2017/0028137 A1* | 2/2017 | Mirabito | A61M 5/425 |
| 2017/0266664 A1* | 9/2017 | Lukhaub | B01L 3/523 |
| 2018/0353954 A1* | 12/2018 | Pennie | G01N 33/491 |

* cited by examiner

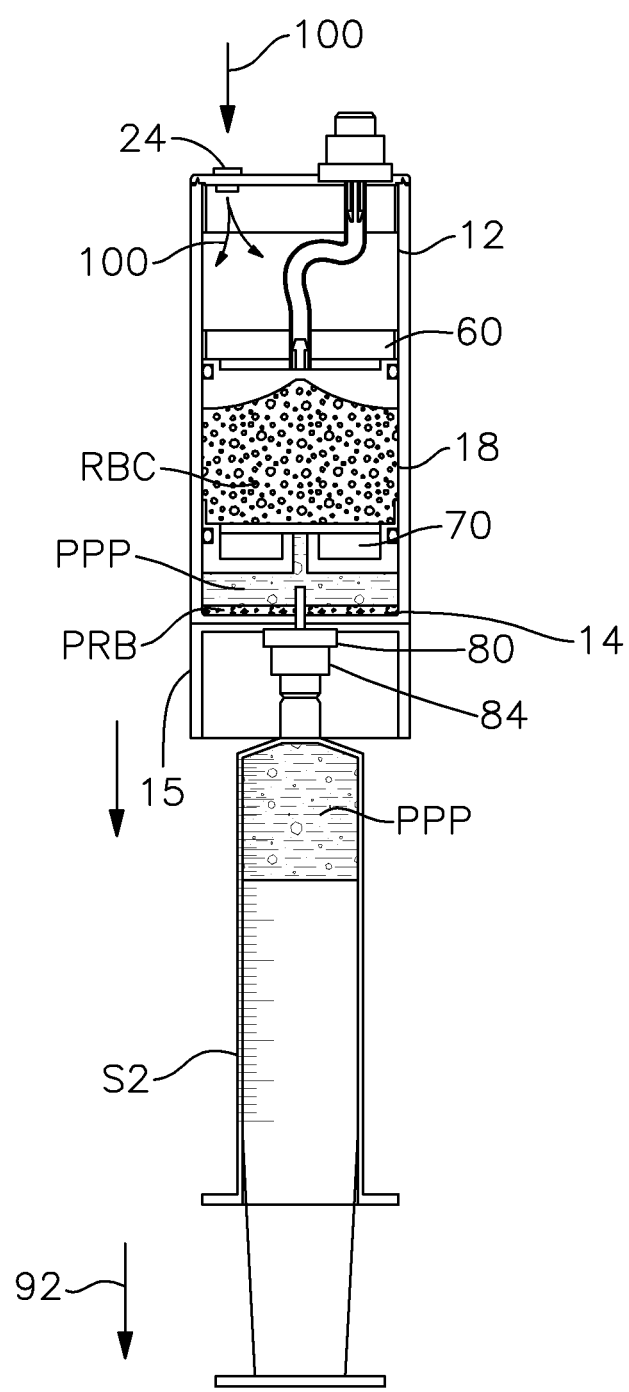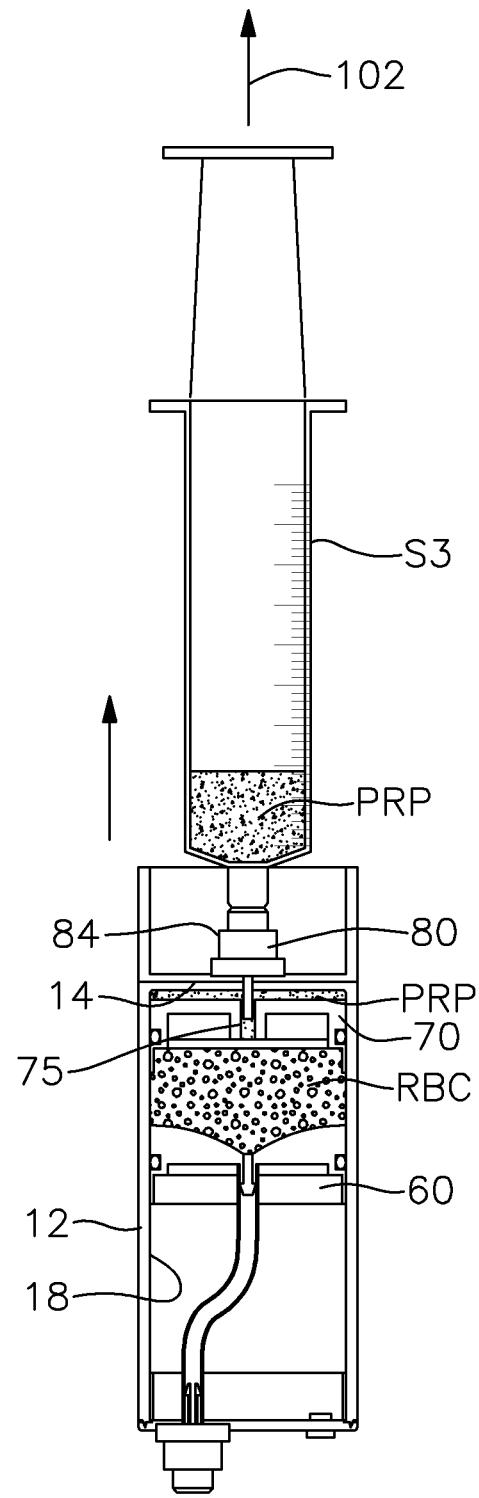
Fig. 9
Fig. 10

DUAL PISTON CENTRIFUGE TUBE

RELATED APPLICATION

This application claims the benefit of U.S. Provisional Application Ser. No. 62/516,755 filed on Jun. 8, 2017.

FIELD OF THE INVENTION

This invention relates to a dual piston centrifuge tube used to effectively separate and concentrate fluid biological products such as blood, stem cells, bone marrow aspirate and the like into constituent components, which may be conveniently and efficiently aspirated following centrifugation. The apparatus is particularly effective for sequestering platelet-rich plasma and bone marrow aspirate for use in surgical, medical and veterinary procedures.

BACKGROUND OF THE INVENTION

Platelet-rich blood plasma is required for use in various medical procedures. This blood product is particularly effective due to its growth promoting features, which assist greatly in wound healing and bone regeneration. Presently, blood plasma with a high concentration of platelets is utilized for dental implants and other periodontal procedures, facial reconstruction, oral or maxillofacial surgery and chronic wound care. In order to obtain a required concentration of platelets, a blood sample normally must be centrifuged in order to separate the blood into its component blood products (i.e. plasma, red blood cells and platelets). The platelets, typically in a form of a white "buffy coat", are then separated from the blood sample and sequestered in concentrated form through aspiration. Conventional aspiration techniques often fail to provide a satisfactory concentration of platelets. Cross-contamination between the constituent products is frequently encountered. I have determined that a continued the need exists for a cost effective apparatus that facilitates the sequestration of platelets and provides for highly pure platelet production, while minimizing cross-contamination between blood components.

I have developed various centrifuge assemblies as disclosed in U.S. Pat. Nos. 6,835,353 and 7,976,796, as well as pending U.S. patent application Ser. No. 14/741,920 to address the foregoing concerns. These products have achieved superior results and proven to constitute a significant improvement over the prior art. Nonetheless, I have determined that further beneficial advancements can be made in centrifuge tube technology. Existing tubes that employ a sliding piston or diaphragm can exhibit an unbalanced operation when centrifuged if blood product is not filled to the capacity of the tube and air is trapped within the tube below the piston. Maintaining an optimal purity of the platelet rich product (PRP) remains a significant concern and the need exists for new and improved ways to protect the PRP from being contaminated by air and other blood components present in the tube. Likewise, the need continues to exist for centrifuge tubes that feature a simpler and failure resistant construction that enables PRP and other constituents of fluid biological products to be obtained in a quick, convenient and reliable manner for use in various surgical, medical and veterinary applications. It is especially important that the components of the fluid product being centrifuged avoid cross contamination as well as airborne contamination.

SUMMARY OF THE INVENTION

It is therefore an object of the present invention to provide a simpler, more efficient and highly reliable dual piston centrifuge tube that allows blood, bone marrow aspirate and other fluid biological products to be effectively separated and concentrated into constituent components and conveniently aspirated following separation.

It is a further object of this invention to provide a dual piston centrifuge tube that enables highly concentrated PRP to be manufactured more efficiently and with greater purity than has heretofore achieved using known technology.

It is a further object of this invention to provide a dual cylinder centrifuge tube which enables the manufacture of improved, highly concentrated and pure PRP in a relatively uncomplicated, quick, efficient, safe and effective manner.

It is a further object of this invention to provide a dual piston centrifuge tube that enables blood product and other fluid biological products to be aspirated in a reliable and extremely simple manner.

It is a further object of this invention to provide a dual piston centrifuge tube that permits a host of chemicals, bodily fluids and other fluid biological products to be separated and individually aspirated with a reduced risk of cross-contamination or airborne contamination.

It is a further object of this invention to provide a dual piston centrifuge tube that is particularly effective for sequestering a high concentration of platelet-rich plasma for use in various medical, surgical and veterinary procedures.

It is a further object of this invention to provide a dual piston centrifuge tube that may be used effectively and efficiently for separating and aspirating a wide range of biological products, including but limited to blood, stem cells, bone marrow aspirate, etc.

It is a further object of this invention to eliminate the unbalanced operation commonly exhibited by known centrifuge tubes during centrifugation by reducing the amount of air trapped in the tube.

It is a further object of this invention to provide a dual piston centrifuge tube featuring a configuration and construction that enables PRP and other biological fluids to be more effectively and completely recovered from the tube following centrifugation.

This invention results from a realization that an improved centrifuge tube, which is especially effective for producing a concentrated PRP of high quality and purity may be achieved by employing a pair of pistons that are slidable through a cylindrical tube and wherein one of the pistons is connected to a common inlet/outlet port formed in the top of the tube and the other piston is disposed in the tube between the upper piston and a second inlet/outlet port formed in the lower end of the tube. This tube may be efficiently and effectively utilized to separate a blood product into its constituent components and to obtain a pure, concentrated and very high quality PRP following centrifugation and aspiration.

This invention features a dual piston centrifuge tube assembly in the form of an elongate tubular receptacle having a lower end and a capped upper end. A single common inlet and outlet port is formed in the capped upper end for communicating with an interior chamber of the tubular receptacle. A second common inlet/outlet port that communicates with the chamber is formed through the lower end of the tubular receptacle. A single, flexible fluid-conducting pipe is communicably connected to the first common inlet/outlet port for extending through the chamber of the tubular receptacle. A first liquid impermeable piston is mounted within the tubular receptacle for sealably engaging an interior surface of a longitudinal sidewall of the tubular receptacle and moving longitudinally through the receptacle. The fluid-conducting pipe is disposed through the first piston such that a distal end of the pipe communicates with the receptacle chamber below the first piston. A second liquid impermeable piston is mounted for longitudinally sliding through the chamber of the longitudinal receptacle between the first piston and a lower end of the receptacle.

Blood product or other fluid biological product to be separated is introduced through the first inlet/outlet port and fluid conducting pipe into the tubular receptacle chamber below the first piston and above the second piston. The first piston is thereby driven upwardly within the tubular receptacle chamber as the fluid is introduced. The tube assembly is then centrifuged a first time to separate the fluid into constituent components. When the fluid includes a blood product, the constituent components may include a lower layer of red blood cells and an upper layer of platelets suspended in plasma. This upper layer is then aspirated through the first common inlet/outlet port, which draws the first piston downwardly through the tube until substantially all of the plasma/platelet suspension is aspirated and the upper piston generally engages the red blood cell layer to constrain the red blood cell layer between the pistons. The aspirated plasma/platelet suspension is then re-introduced into the chamber of tubular receptacle through the second inlet/outlet port. This drives the first and second pistons as well as the constrained red blood cells, between the pistons upwardly through the tubular receptacle until the re-introduced plasma/platelet suspension fills the tubular receptacle between the lower piston and the lower end of the tubular receptacle. The tube assembly is then centrifuged a second time. This separates the plasma/platelet suspension into an upper platelet poor plasma layer and a lower platelet rich buffy coat layer. At least a portion of the upper platelet poor plasma layer is aspirated from the tubular receptacle through the second common inlet/outlet port. The platelet rich buffy coat layer may then be re-suspended within the platelet plasma suspension remaining in the tubular receptacle to produce a platelet rich plasma (PRP) which is aspirated from the tubular receptacle through the second inlet/outlet port and attached tubular stem.

In a preferred embodiment, the first and second inlet/outlet ports may include respective first and second self-sealing valve ports. The upper end of the tubular receptacle may be sealed closed or include a removable cap. In either case the upper end of the tubular receptacle preferably carries a barbed or other connective inlet element for communicably interengaging the first valve port and the fluid conducting pipe. The first and second pistons may be sealably interengaged with the interior surface of a sidewall of the tubular receptacle by respective O-rings. The second inlet/outlet port may include a tubular conduit or stem that extends upwardly from a flat floor at the lower end of the receptacle into the chamber between the second piston and lower end of the receptacle. The second piston preferably has a flat bottom for flushly engaging the flat floor of the lower end of the tubular receptacle. The flat bottom of the second piston may feature a cylindrical receiving hole or channel for receiving the tubular stem that extends upwardly from the floor of the tubular receptacle. This allows the flat bottom of the second piston to flushly interengage the flat floor of the tubular receptacle during use of the centrifuge tube. The second piston may alternatively include a tapered, conical or concave, bottom surface for receiving the stem.

After the second centrifugation is performed and the plasma/platelet suspension or other fluid product is separated into two discrete layers, the majority of the upper layer (e.g. platelet poor plasma) may be aspirated through the tubular stem, which is configured to extend to a level above the lowermost constituent layer (e.g. the platelet rich buffy coat) and is connected communicably through the second valve port. The tube may then be swirled or otherwise agitated to re-suspend the platelet rich buffy coat in the remaining plasma. The tubular receptacle may then be inverted and aspiration may be repeated to retrieve the re-suspended platelet rich plasma remaining in the tubular receptacle between the second piston and the second inlet/outlet port. Such aspiration pulls the second piston upwardly through the receptacle chamber until the flat bottom surface of the second piston flushly engages the flat floor at the lower end of the tubular receptacle. As a result, all or substantially all of the PRP remaining in the tubular receptacle is successfully aspirated through the tubular stem and second valve port such that a highly concentrated PRP is obtained. In cases where the second piston has a concave or tapered bottom surface, aspiration is performed until the concave or tapered surface engages the tip of the stem. This configuration also allows for most of the PRP to be recovered following centrifuging of the subject.

A vent may be formed in the upper end of the tubular receptacle for equalizing the air pressure within the tubular receptacle as fluid is added to or removed from the receptacle. The vent may carry a filter for removing contaminants from the air that is introduced into the tubular receptacle during aspiration. All ambient air drawn into the tubular receptacle during use of the tube is retained in an upper portion of the receptacle chamber, above the first piston. At all times, the space within the receptacle between the second piston and the second inlet/outlet port remains sealed against and substantially devoid of ambient air. The plasma and suspended platelets accommodated within the receptacle chamber between the second piston and the lower end of the receptacle thereby remain fully enclosed and sequestered from any and all air entering the vent by the upper and lower pistons and the intermediate layer of red blood cells or other fluid product contained between the pistons. This minimizes the risk of airborne contamination of the platelet rich plasma. It also eliminates air from the lower end of the tubular receptacle so that the tube maintains a low center of gravity and imbalance during centrifugation is avoided.

BRIEF DESCRIPTION OF THE DRAWINGS

Other objects, features and advantages will occur from the following description of a preferred embodiment and the accompanying drawings, in which:

FIG. 9 is an elevational, cut-away and partly cross sectional partly side view depicting aspiration of the PPP from the tubular receptacle;

FIG. 10 is an elevational, cut-away and partly cross sectional side view illustrating aspiration of the platelet rich plasma (PRP) from the tubular receptacle after the lower buffy coat layer has been re-suspended in the plasma remaining in the receptacle.

DETAILED DESCRIPTION OF PREFERRED EMBODIMENTS

Figure 1:
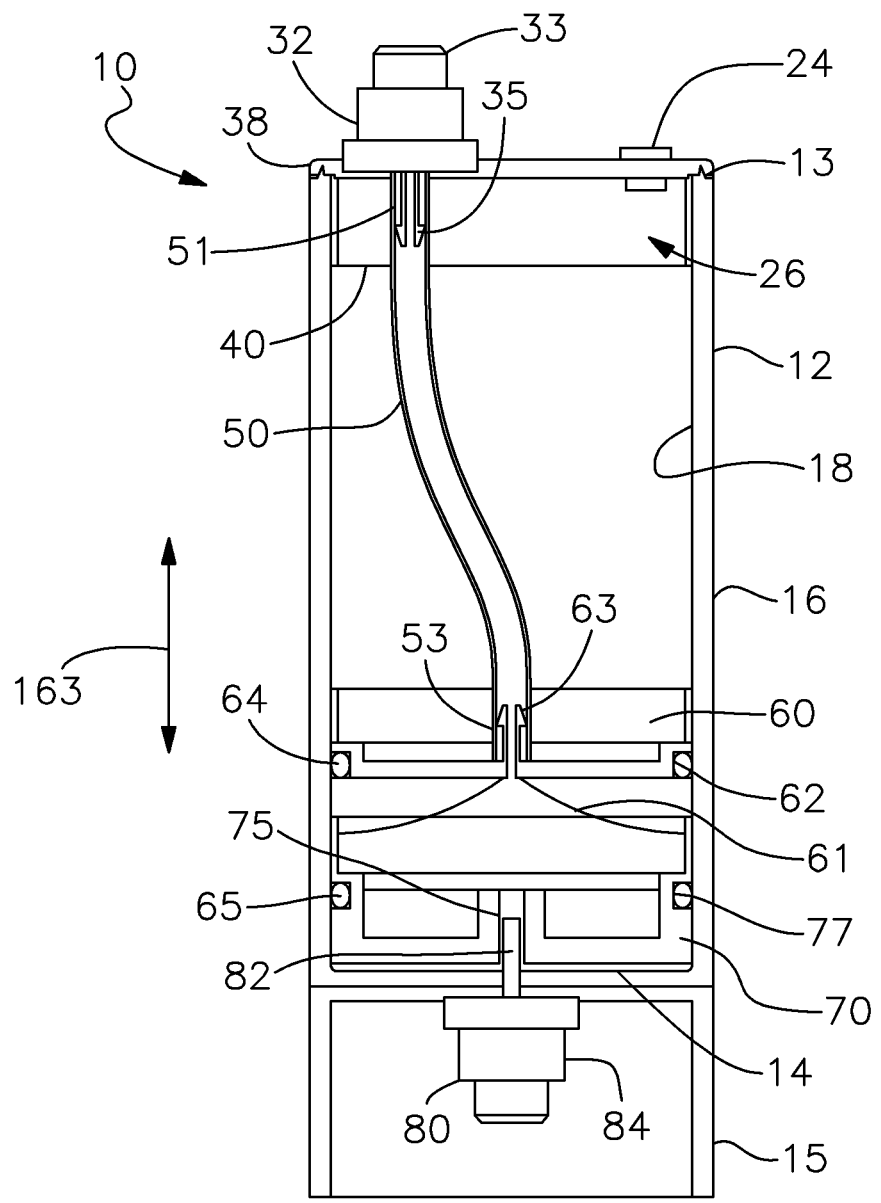
FIG. 1 is an elevational, cut away side view of a preferred dual piston centrifuge tube in accordance with this invention without any fluid or other biological product within the tubular receptacle.
Figure 1A:
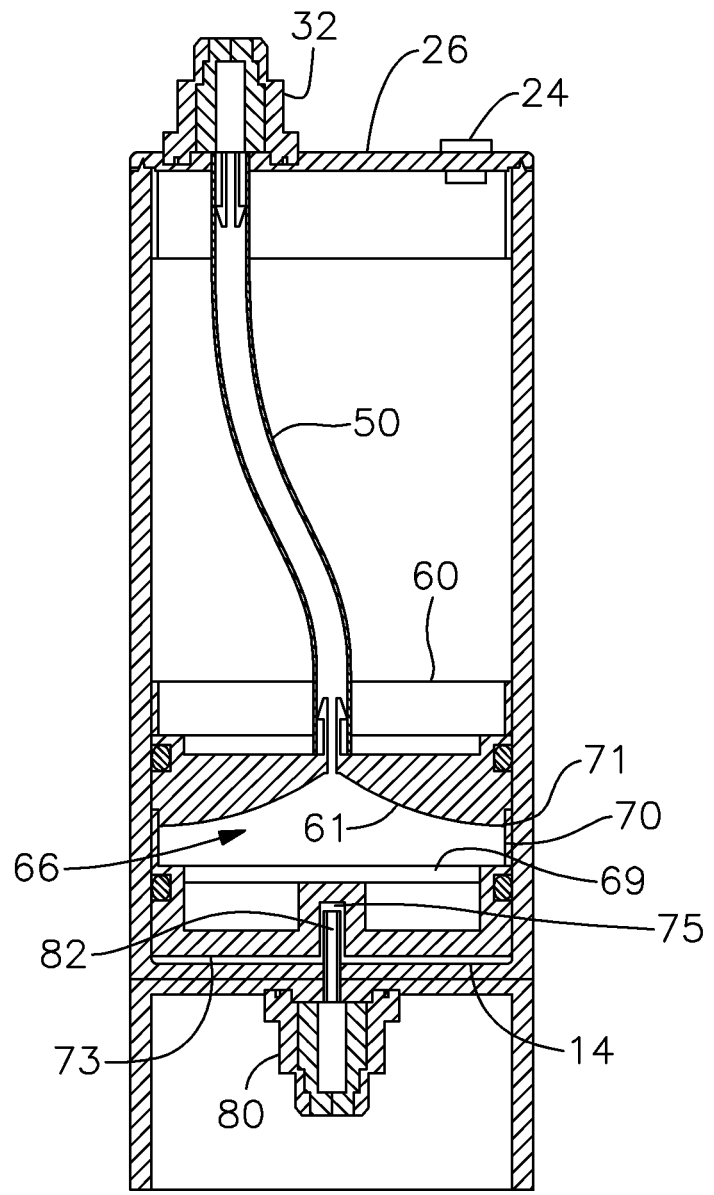
FIG. 1A is an elevational, cross-sectional view of the tube.
Figure 2:
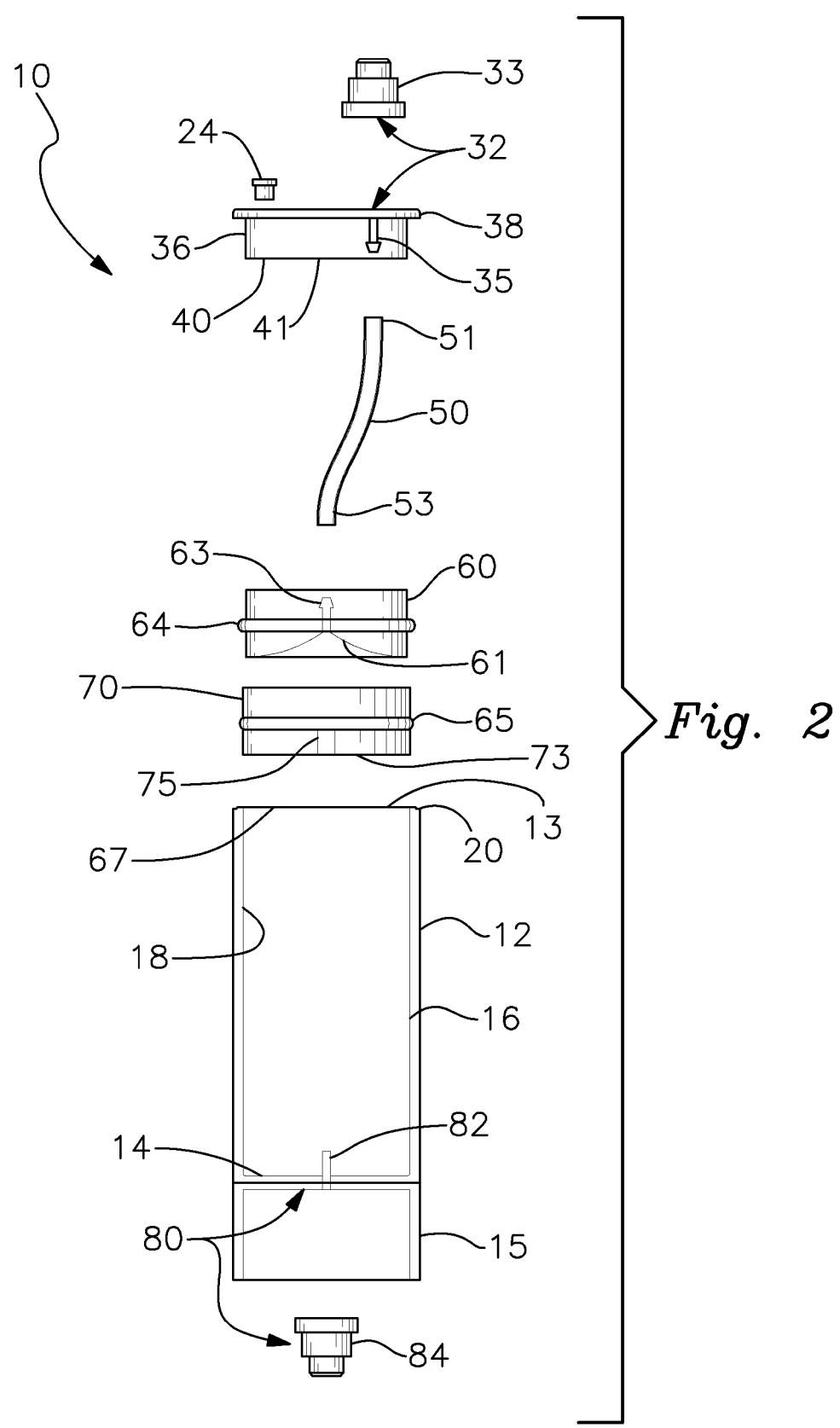
FIG. 2 is an exploded, cut away and partly cross-sectional side view of the tube.

There is shown in FIGS. 1, 1A and 2 a dual piston centrifuge tube 10 that includes a tubular or cylindrical receptacle 12 having an upper end 13 and an opposite lower end 14 comprising a preferably flat floor. The upper end is shown open in FIG. 2, but is capped during usage of the tube, as depicted in FIG. 1. A cylindrical sidewall 16 extends longitudinally between lower end 14 and upper end 13. Tubular receptacle further includes an interior chamber 18 that extends from the lower end to the upper end of the receptacle. This chamber accommodates blood, chemicals, stem cells, bone marrow aspirate or other biological fluids/products to be centrifuged and aspirated using assembly 10.

As used herein, "centrifuge tube" and "tube" should be understood to comprise various shapes and sizes of vessels, receptacles and containers having an interior chamber for holding a fluid biological product and capable of being centrifuged to separate the product into constituent components. The dual piston centrifuge tube is not limited to just tubular and elongate configurations, although such configurations will typically be used in preferred embodiments of this invention.

As best shown in FIG. 2, an annular notch 20 is formed at the upper end of sidewall 16. This notch enables an upper end cap or lid 26 to securely and sealably interengage receptacle 12 as will be further described below. Lower end 14 of receptacle 12 comprises a floor 22 that defines the bottom of interior chamber 18. A cylindrical skirt 15 is connected unitarily with and depends from lower end 14 of receptacle 12 and sidewall 16. The cylindrical skirt acts as base, which stably supports the tubular receptacle in an upright condition on a table or other flat or horizontal surface. In this way, the centrifuge tube assembly does not require a separate rack or holder for support. Cylindrical skirt 15 also securely supports the device upright in a standard centrifuge machine when the tube is centrifuged in accordance with the orientation depicted in FIGS. 4 and 8 and as described below.

Tubular receptacle 12 is typically composed of a durable plastic material such as polypropylene or other material suitable for medical or veterinary applications. The tube should also be constructed to withstand the forces exerted by centrifuging. In certain applications, shatter resistant glass may be employed.

A plurality of graduated volume markings, not shown herein but see U.S. Pat. No. 7,976,796 (hereinafter Pat. No. '796), may be formed at various selected intervals along the exterior sidewall of tubular receptacle 12. Such markings should be formed at heights or intervals corresponding to commonly selected volumes of biological product that will be introduced into the tube. Such markings may be varied within the scope of this invention.

A vent 24 is formed through cap 26 to communicably interconnect chamber 18 with the ambient air surrounding tube assembly 10. Vent 24 is analogous to the vents disclosed in Pat. No. '796 and US Publication No. 2016/0367982 (hereinafter Pub. No. '982) with the exception that the vent is formed at the upper end or cap of the tube assembly rather than through the bottom of the tubular receptacle as disclosed in the published application. As in Pub. No. '982, vent 24 may comprise a vent plug that fits through a hole in the cap to define a pressure equalizing or neutralizing vent in receptacle 12. Vent 24 may feature a through channel that accommodates a filter for trapping contaminants that are pulled into receptacle 12 with the ambient air during operation of the tube as described below. Once again, this filter construction may be of the type disclosed in the above-referenced published application.

In preferred versions of this invention, cap 26 is permanently secured to the tubular receptacle. This may be accomplished by ultrasonic welding or other known methods. The upper end of the receptacle may also be closed by a cap or lid that is molded or otherwise formed unitarily with the cylindrical receptacle using techniques known to persons skilled in the art. Alternatively the end cap may be releasably engaged with open end 13 of receptacle 12. Cap 26 may include a generally cylindrical shape that conforms the cross sectional shape of the receptacle. The cap features a generally flat upper lid 38 having a circular shape that generally matches the circular cross sectional shape of receptacle 12. Vent 24 is formed through a matching hole in lid 38. An annular or cylindrical flange 40 is attached unitarily to and depends from lid 38. Flange 40 surrounds a pocket 41 within cap 26. The pocket may at least partially accommodate a flexibly collapsible fluid conducting aspiration pipe 50 when fluid is introduced into receptacle 12 though the aspiration pipe and the pipe collapses. This is described more fully below. The flange is configured and sized such that it can be slid snugly and securely into interior chamber 18 of receptacle 12 after the internal components of the tube are installed, as shown in FIG. 1. This effectively closes the receptacle so that it may be used in the manner disclosed herein. Lid 38 includes a peripheral lip (not shown in FIG. 1 but see the peripheral lip disclosed in my co-pending application Pub. No. '982). This lip interengages the peripheral notch 20 formed at upper end 13 of receptacle 12 when cap 26 is inserted into chamber 18. In this state, cap 26 is securely and snugly engaged with the receptacle. The interconnection is tight enough or the cap is otherwise permanently joined to sidewall 16 so that the cap remains in secure, seated interengagement with the upper end of the receptacle during centrifuging of tube 10 and subsequent fluid aspiration therefrom.

A first common inlet/outlet port 32 is formed in receptacle 12 through lid 38 of cap 26. More particularly, the first or upper inlet/outlet port may comprise an exterior self-sealing valve port section 33, as shown in FIGS. 1 and 2, and a barbed port portion 35 connected interiorly to cap 26 and depending from lid 38 into pocket 41. The exterior self-sealing valve port section 33 and the interior barbed port section 35 are themselves communicably interconnected to one another through lid 38 of cap 26. Various alternative types of inlet/outlet port constructions may be utilized. The first port 32 should be capable of being exteriorly interengaged by a syringe to either inject and introduce fluid into tubular receptacle 12 or to aspirate fluid from the tubular receptacle, as required. These operations are described more fully below.

Various alternative and/or analogous forms of construction for the upper end cap and common inlet/outlet port are disclosed in U.S. Pat. No. 6,835,353 (hereinafter Pat. No. '353) and Pat. No. '796 as well as Pub. No. '982, the disclosures of which are incorporated herein by reference. Preferably, cap 36 as well as inlet/outlet port 44 are likewise composed of polypropylene or other material similar to that forming the tubular receptacle itself. The common inlet/outlet port may be molded together with the cap in a single manufacturing process or formed as separate components which are assembled in the manner described herein. Assorted types of integral and separated inlet/outlet ports may be utilized including luer type ports as are described in U.S. Pat. Nos. '353 and '796 and the published application referenced above.

As previously described, vent 24, FIGS. 1 and 2, is formed through cap 26 adjacent first inlet/outlet port 32. This vent maintains a stable neutral pressure within tubular receptacle 12 during the aspiration process. The vent may be formed at various other locations in the capped upper end. It is important for vent 24 to be formed in the upper end so that tube 10 remains balanced during the centrifuge operation.

Flexible aspiration pipe 50 is communicably interengaged at its upper end 51 with barbed section 35 of first or upper port 32. The pipe is composed of a flexible yet strong plastic material such as silicone that permits the pipe to be reliably flexed or collapsed during operation of tube 10.

A first or upper generally disk-shaped sealing diaphragm or piston 60 is attached to the lower or distal end of pipe 50. Piston 60 is liquid impermeable and slidably mounted for longitudinal movement within chamber 18 of tubular receptacle 12. First piston 60 has a generally circular or cylindrical peripheral shape conforming to the interior shape of sidewall 16. The piston features an annular peripheral groove 62 for accommodating an O-ring or alternative seal 64, which sealingly and slidably interengages the interior surface of sidewall 16 of tubular receptacle 12. This allows piston 60 to move longitudinally through chamber 18 during operation of tube assembly 10 as indicated by double headed arrow 163 in FIG. 1. As best indicated in FIGS. 1 and 2, the lower or distal end 53 of aspiration pipe 50 communicably interengages a channel fitting 63 formed centrally through piston 60 from the top surface to the conically configured or otherwise concave bottom surface or discharge end 61 of piston 60. The distal end 53 of pipe 50 thereby communicates with an interior portion 66 of receptacle 12. See FIGS. 1A, 3 and 5 below piston 60.

A second or lower liquid impermeable piston 70 is likewise mounted for slidable movement longitudinally through chamber 18 of receptacle 12. Piston 70 again includes a cylindrical wall 71 conforming to the interior of receptacle sidewall 16 and peripherally configured similarly to first piston 60. The second piston further includes an annular groove 77 for accommodating an O-ring or other sealing component 65 that sealably engages the interior wall of receptacle. A first, upper circular plate 69 of piston 70 is attached to and extends interiorly across cylindrical wall 71. A second, lower circular and flat plate 73 is similarly carried by wall 71 to form a flat bottom surface of piston 70. A cylindrical receiving channel 75 is formed in the bottom of piston 70 and extends between plates 69 and 73. The lower end of channel 75 extends fully through plate 73 or otherwise communicates with a hole or opening in the plate forming the bottom surface of piston 70, Unlike first piston 60, the second piston is not connected to an aspiration pipe. Pistons 60 and 70 may be constructed in alternative ways that perform the functions and achieve the results exhibited by the structure disclosed herein. One or more of the pistons may be configured and constructed similarly to the pistons/diaphragms shown in U.S. Pat. No. '796 and US Pub. No. '982 respectively. Instead of the cylindrical receiving channel 75 shown herein, the second piston 70 may include a tapered bottom surface generally having the shape of a truncated cone, which operates as described below.

A lower, second common inlet/outlet port assembly 80 is operatively connected to the lower end 14 of tubular receptacle 12. In particular, inlet/outlet port 80 includes a tubular conduit or stem section 82 that is formed through lower end 14 and extends upwardly into the interior chamber 18 of tubular receptacle 12. The second inlet/outlet port also includes a self-sealing valve port section 84 that is analogous to previously described self-sealing port section 33 of first port 32. Valve port section 84 is attached to the exterior surface of lower end 14 and communicatively connected through lower end 14 to stem section 82. Valve port section 84 depends from the lower end into the space surrounded by supportive skirt 15. See FIG. 1. Stem section 82 is aligned with receiving channel 75 of piston 70 and includes a length that allows it to fit into receiving channel 75, as shown in FIG. 1, when the second piston is driven to the lower end 14 of receptacle 12 during operation of assembly 10. This is described more fully below. Second port assembly 80 may again comprise a luer type port as known in the art.

Prior to usage of assembly 10, sealing pistons 60 and 70 are typically positioned within chamber 18 of receptacle 12 proximate the lower end 14 of the receptacle. See FIG. 1. In certain embodiments, the tube assembly may be constructed to include a removable cover at the upper end as shown, for example, in co-pending application Pub. No. '982. Moreover, respective closures, as disclosed in the referenced Pat. No. '796 and Pub. No. '982, may be employed to cover the respective inlet/outlet valves 32 and 80. Such covers and closures may be utilized in order to further isolate and enclose chamber 18 and to further reduce the risk of fluid contamination during the use of assembly 10. Nonetheless, the present invention may be practiced effectively without the use of such covers and closures due to the use of self-sealing valve sections 33 and 84.

Assembly 10 is utilized to centrifuge a fluid biological product into its constituent components and then to aspirate one or more of those components as shown in FIGS. 3-11. A preferred representative use for dual piston centrifuge tube assembly 10 is the separation of a blood sample into constituent blood components. Typically, it is desirable to separate plasma, and ultimately platelets, from red blood cells of a blood product such that a highly concentrated platelet rich blood product may be used effectively in various surgical, medical or veterinary applications. This process is performed using assembly 10 in the following manner.

Figure 3:
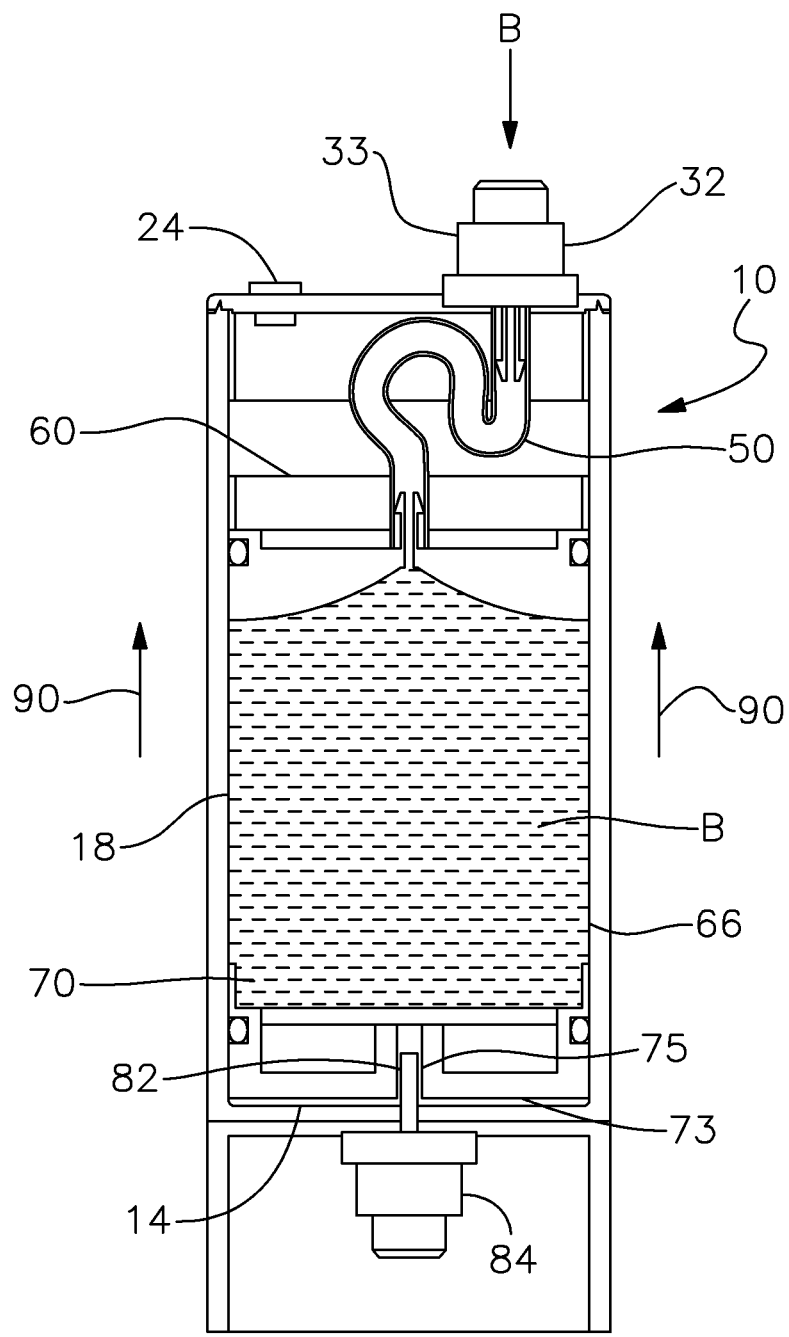
FIG. 3 is an elevational, cut away and partly cross-sectional side view of the dual piston centrifuge tube after a blood product has been introduced into the tube to drive apart the upper and lower pistons.

Initially, the empty receptacle 12 is stood upright on its cylindrical base or skirt 15 upon an underlying table or platform. If any covers or closures are engaged with the tube assembly or ports respectively, such covers/closures are removed. Blood product B is then introduced into the interior chamber 18 of tubular receptacle 12. Specifically, a 60 ml or other sized hypodermic syringe containing the blood or other biological product is operably engaged with the first or upper self-sealing valve section 33 in a standard manner. See U.S. Pat. Nos. '353 and '796 and Pub. No. '982. Valve section 33 holds the dispensing tip of the syringe in place so that the hypodermic syringe is securely engaged with tube 10. As shown in FIG. 3, the syringe is then operated in a conventional manner to inject and introduce the blood product B to be separated through port 32 and flexible aspiration pipe 50 into the interior chamber 18 of receptacle 12. More particularly, blood product or other biological product B is transmitted through pipe 50 and first sealing piston 60 into the space 66 of chamber 18 between upper piston 60 and second, lower piston 70. As blood B is introduced into space 66 (FIG. 3) the increasing volume of blood pushes piston 60 upwardly as indicated by arrows 90. Blood product is added to the receptacle by the syringe in this manner until the selected level of fluid is introduced into the tube. As first piston 60 rises within chamber 18 in response to the rising volume of blood B, that piston remains in sealing engagement with the interior sidewall 16 of receptacle 12. Flexible pipe 50 (see also FIGS. 1 and 2) bends and collapses within the tubular receptacle 12. Air in chamber 18 above piston 60 is expelled by the rising piston through vent 24. When a selected or desired volume of blood has been added to the receptacle, the syringe is disengaged from port 32 of assembly 10. For human blood work, the selected volume of blood may be, for example, 50 and 60 ml. This volume is preferred because it typically yields approximately 7 ml of platelet rich blood. Using the dual piston assembly of this invention yields a highly concentrated and high quality PRP.

Figure 4:
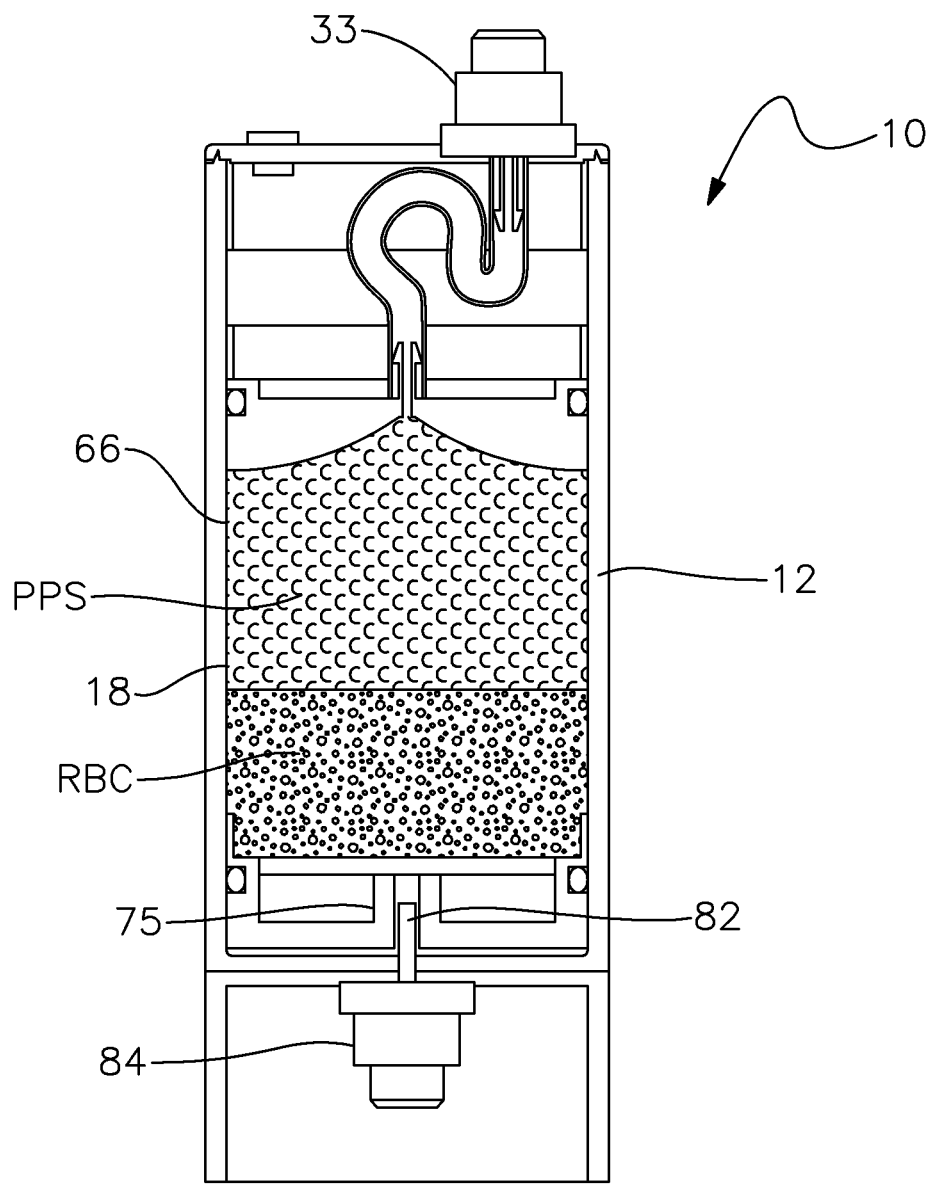
FIG. 4 is an elevational, cut away and partly cross-sectional side view of the tube after it has been centrifuged a first time to separate a platelet/plasma suspension from red blood cells into respective layers between the pistons.

After the desired amount of blood product or the biological product is introduced into the tubular receptacle, the syringe is disengaged from port 32. The upper port and upper end of the tube may then be covered by an exterior cover or closure, although the self-sealing valve port section 33 typically allows centrifuging to be performed without such closures. Tubular receptacle 12 is then placed in a centrifuge and counterbalanced by another tube placed in the centrifuge machine. Skirt 15 allows tube assembly 10 to sit stably within the centrifuge. Moreover, the second, lower piston 70 is maintained securely against the lower end 14 of receptacle 12. As a result, little or no air is trapped at the lower end of chamber 18. This allows the tube to effectively remain balanced while it is being centrifuged. The tube is centrifuged for approximately 90 seconds (although this time as well as the speed of the centrifuge may be varied within the scope of this invention in a manner known to persons skilled in the art) and, as shown in FIG. 4, blood B is separated within space 66 into an upper layer comprising largely platelet/plasma suspension PPS of plasma and a lower layer RBC comprising primarily red blood cells. At this stage, at least 90% of the red blood cells in the blood product separate from the platelets and plasma and settle within layer RBC. Various known types of centrifuge machines may be employed for the initial centrifuging. A single round or multiple rounds of centrifuging may be utilized at this stage.

Figure 5:
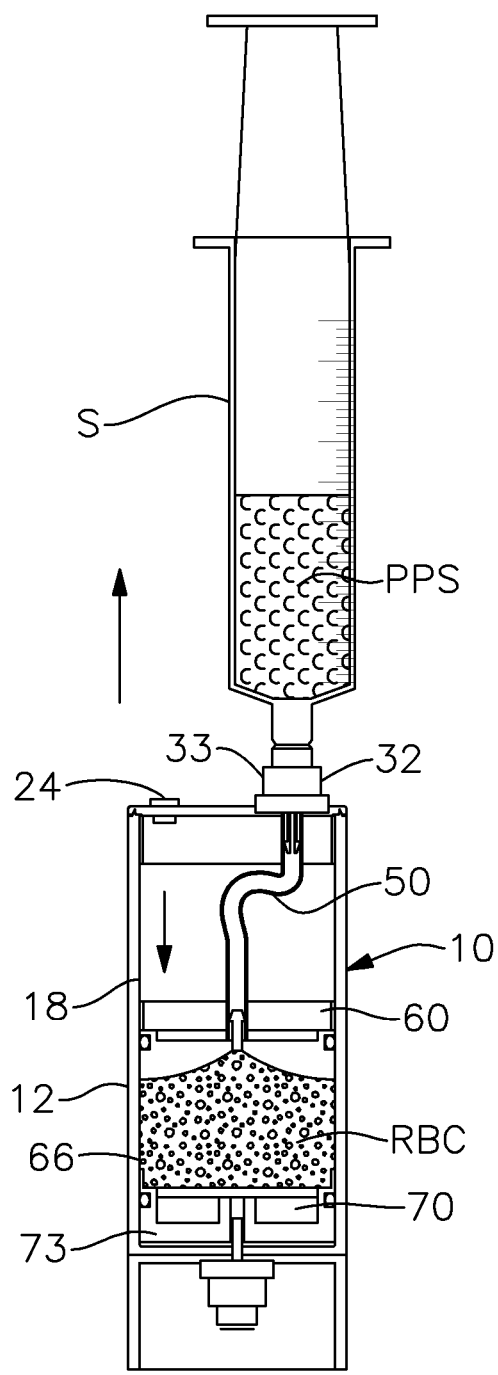
FIG. 5 is an elevational and cut-away side view depicting the upper plasma layer being aspirated from the tube to leave behind the lower red blood cell layer.

After the first centrifuging stage is completed, tube 10 is removed from the centrifuge and again supported on its flat base or skirt 15. Both layers PPS and RBC are held securely between the separated upper and lower pistons 60 and 70. As shown in FIG. 5, a syringe S is then engaged with self-sealing valve port section 33 of port 32. Syringe S is drawn to aspirate the platelet plasma suspension PPS from space 66 of interior chamber 18 into syringe S. The PPS is drawn through pipe 50 and port 32 into syringe S. Ambient air is drawn into chamber 18 through vent 24 and upper piston 60 is driven downwardly through chamber 18 of receptacle 12. At the same time, aspiration pipe 50 expands or extends through interior chamber 18. Aspiration is continued in this manner until the upper piston generally reaches the boundary between the PPS and RBC layers. Syringe S is then disengaged from port 32 and the red blood cells remain segregated and constrained in space 66 between upper piston 60 and lower piston 70.

Figure 6:
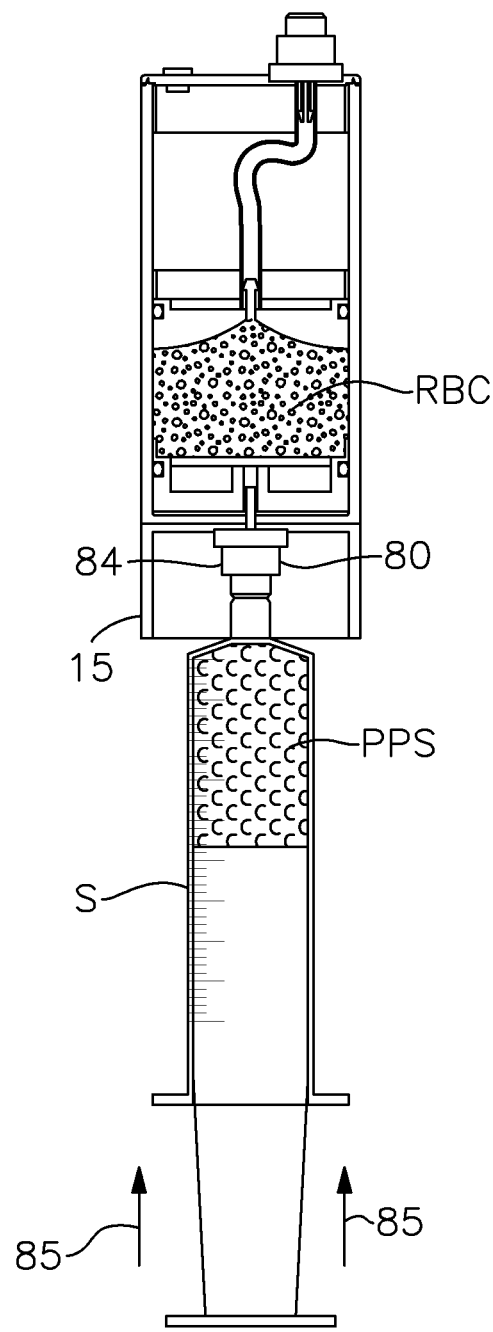
FIG. 6 is an elevational and partly cut-away side view showing a syringe that carries the previously aspirated PPS being engaged with the plasma port so that PPS may be injected into the tubular receptacle.
Figure 7:
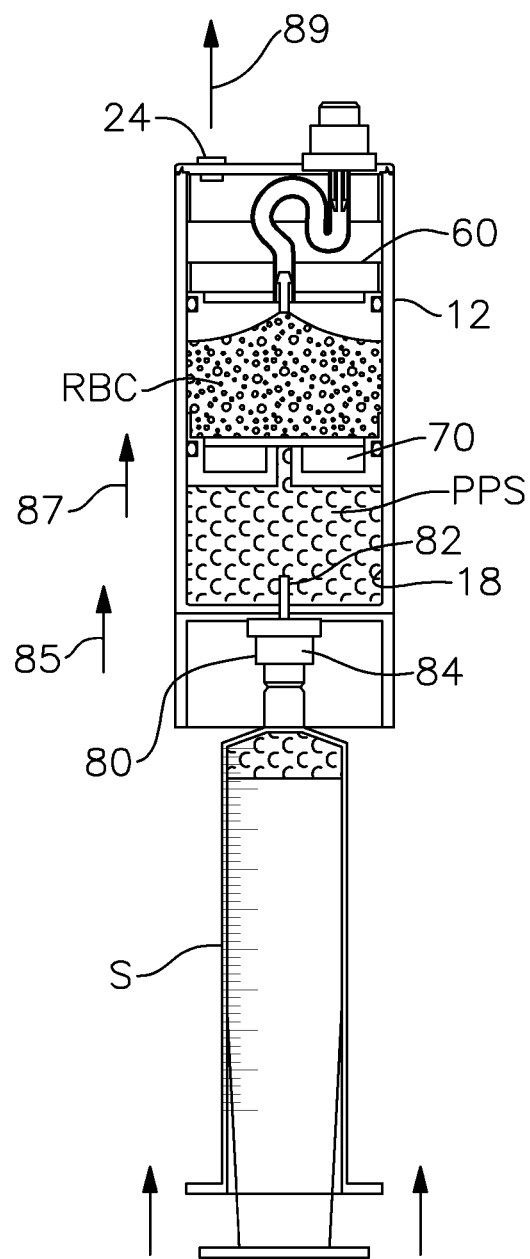
FIG. 7 is an elevational, cut-away, partly cross sectional view illustrating injection of the PPS into the tubular receptacle such that both pistons are driven upwardly through the receptacle.

As shown in FIG. 6, PPS accommodating syringe S is next engaged with the self-sealing valve port section 84 of second inlet/outlet port 80 located within the area surrounded by supportive skirt 15. The syringe is then depressed as shown by arrows 85 in FIGS. 6 and 7 so that the PPS in the syringe is injected into chamber 18 of receptacle 12. Specifically, the PPS is introduced through self-sealing port section 84 and stem 82 into the bottom of chamber 18. Lower piston 70, upper piston 60 and the layer of red blood cells RBC held between pistons 60 and 70 are all driven upwardly through receptacle 12, as indicated by arrow 87. The air previously drawn into the upper portion of chamber 18 during the initial aspiration step is thereby expelled outwardly through vent 24 as indicated by arrow 89.

Figure 8:
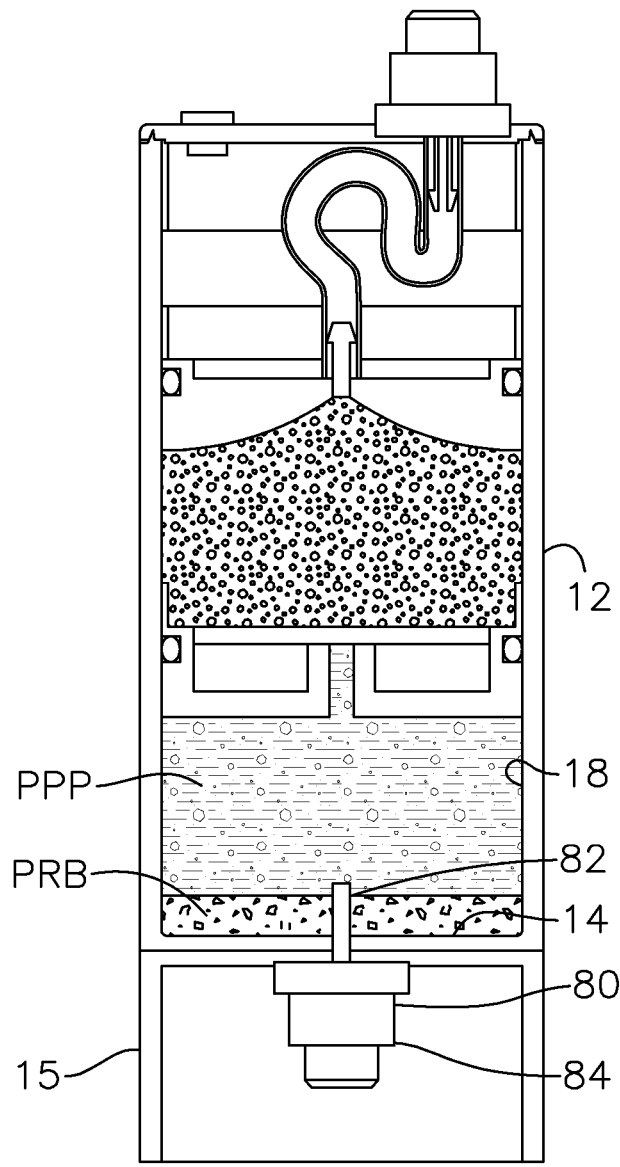
FIG. 8 is an elevational, cut-away and partly cross sectional view of the tubular receptacle after it has been centrifuged a second time such that the PPS is separated into an upper layer of platelet poor plasma (PPP) and a lower layer of platelet rich buffy coat.
Figure 11:
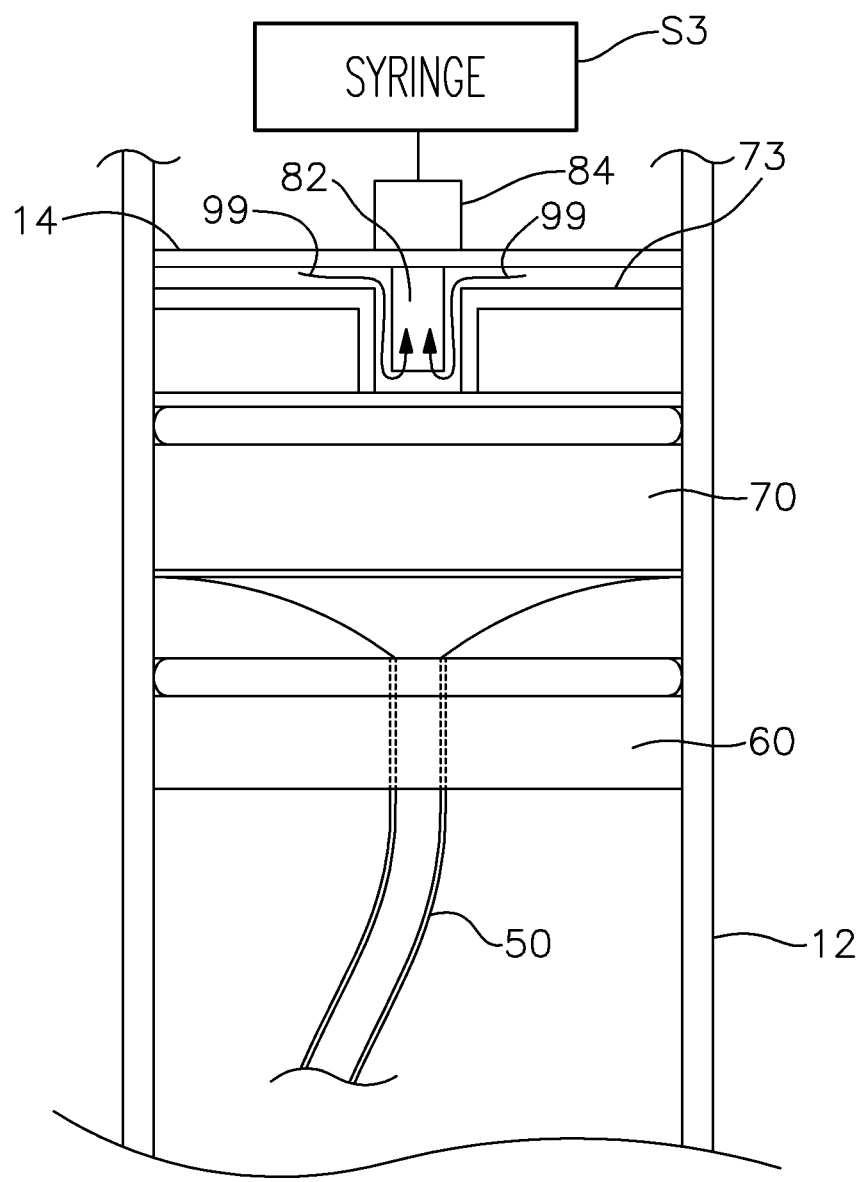
FIG. 11 is a simplified diagrammatic view of the lower end of the tube as PRP is being withdrawn from the tube and with the pistons juxtaposed and the second piston flushly interengaging the flat floor of the tubular receptacle.

When all of the PPS is injected into receptacle 12, syringe S is disengaged from the second inlet/outlet port 84 and receptacle 12 is again placed in a centrifuge assembly. The tube is centrifuged for approximately 5 minutes. Once again, this time may be varied within the scope of this invention. For both centrifuging steps, centrifuge speeds and times may be adjusted in a manner that will be understood to those skilled in the art. As shown in FIG. 8, the PPS injected into chamber 18 is separated by the second centrifuge operation into an upper layer of platelet poor plasma PPP and a lower layer of platelet rich buffy coat PRB. Stem 82 of second inlet/outlet port 80 is sufficiently long enough to extend into the PPP layer. The heavier PRB layer is formed at the lower end 14 of receptacle 12. Stem 82 extends upwardly from lower end 14 of receptacle 12 such that the tip of stem 82 is disposed in the PPP layer.

As illustrated in FIG. 9, a second syringe S2 is interengaged with self-sealing valve section 84 of second inlet/outlet 80 within the area surrounded by supportive skirt 15. The plunger of the syringe is then retracted as illustrated by arrow 92. This aspirates PPP fluid from chamber 18. PPP is aspirated from receptacle 12 into syringe S2 until a total of approximately 7 ml of fluid, consisting of 6 ml PPP and 1 ml PRB, remains in chamber 18 below second piston 70. These are typically the amounts remaining when an initial blood product volume of 50-60 ml is subjected to the two stage centrifugation process in tube 10 as described above. Respective volumes may vary somewhat within the scope of this invention. As PPP is aspirated from tubular receptacle 12, ambient air is again drawn into the chamber 18 through vent 24 in the manner indicated by arrows 100. Both sealing pistons 60 and 70, as well as intermediate red blood cells RBC are pulled or drawn downwardly together through the tubular receptacle. The remaining PPP and PRB layers within chamber 18 are therefore constrained between lower piston 70 and the lower end 14 of receptacle 12.

Syringe S2 containing the aspirated PPP is disengaged from port 80. The platelets of the (e.g. 1 ml) platelet rich buffy coat PRB are then re-suspended in the remaining (e.g. 6 ml) PPP layer contained in receptacle 12. This is typically accomplished by swirling or otherwise gently agitating the tubular receptacle so that the platelets of fluid layer PRB are effectively re-suspended into the plasma of layer PPP. This produces a resulting volume of approximately 7 ml of pure and concentrated platelet rich plasma (PRP).

Following resuspension of the buffy coat in the platelet poor plasma to produce the desired PRP, receptacle 12 is inverted in the manner shown in FIG. 10. This positions supportive skirt 15 and second port 80 at the upper end of the tubular receptacle. The operator then operatively connects a new syringe S3 to the self-sealing valve port section 84 of port 80. The plunger of syringe S3 is retracted as indicated by arrow 102. This aspirates the PRP remaining in chamber 18 between second piston 70 and the lower (now effectively upper) end 14 of receptacle 12. Specifically, the second aspirating operation pulls pistons 60 and 70, as well as intermediate red blood cells RBC upwardly together toward end 14. The PRP produced by the previously described resuspension is supported by the underlying flat plate 73 of piston 70, which now faces upwardly. Piston 70 is pulled upwardly toward flat bottom 14 until the channel 75 receives stem 82. The flat bottom of plate 73 flushly engages the flat bottom 14 of receptacle 12 See FIG. 11. As a result, virtually all of the PRP (approximately 7 ml) contained in the receptacle is aspirated through stem 82 and valve port section 84 into syringe S3 as indicated by arrows 99. This PRP has an extremely high platelet concentration and purity (e.g. approximately 80% or more). The aspirated PRP may then be utilized effectively for desired surgical, medical and veterinary applications.

In embodiments wherein the lower piston features a tapered or truncated conical bottom surface, piston 70 is pulled upwardly during the final aspiration step until the lowermost point or bottom of that concave surface touches the tip of the apparatus stem. This likewise enables the user to retrieve greater amounts of PRP from the tube than has been obtained using prior art devices. Nonetheless, utilizing the disclosed version featuring a second piston with a flat bottom and a receptacle with a corresponding flat bottom, as well as a tubular stem and complementary receiving channel typically enables the user to achieve even greater recovery of high quality PRP.

Not only does centrifuge tube assembly 10 produce a concentrated, pure and high quality PRP in the manner described above, it also does so extremely efficiently and while providing for improved balanced centrifuge operation. Blood product and other biological fluids may be quickly, conveniently and successfully separated into constituent components through a multiple stage separation process that does not require the use of multiple or complex centrifuge tubes. Only a single, dual piston centrifuge tube, as disclosed herein, is needed to obtain a concentrated, pure and high quality PRP or other desired biological fluid. Manufacturing and inventory costs, centrifuge tube complexity and PRP process times are reduced. Simplicity and efficiency are improved considerably.

Centrifuge tube assembly 10 also enables much more balanced, stable and effective centrifuge operation. By providing air vent 24 in the upper end of tubular receptacle 12, any air introduced into the tube remains in the upper end of the tube while the tube is centrifuged. During the first centrifuge step, the lower piston 70 remains engaged with the lower end 14 of receptacle 12. During the second centrifuge step, fluid fills the entire volume of chamber 18 between second piston 70 and lower end 14 of receptacle 12. In both cases, the lower portion of the tubular receptacle is completely evacuated and free of air. As a result, the center of gravity of the tube assembly remains near the lower end of the tube. If any air is present in chamber 18 it is located above first piston 60, which allows the tubular receptacle to maintain a low center of gravity. The tubular receptacle therefore maintains a stable and balanced condition as it is being centrifuged.

It should be further understood that the dual piston centrifuge tube of this invention may employ assorted features and components as depicted in the above referenced devices shown in U.S. Pat. Nos. '353, '796 and Pub. No. '982. Moreover, various other modifications may be made within the scope of this invention. For example, the vent and/or one or both of the common inlet and outlet ports may be formed in the sidewall of the tubular receptacle. The terms "upper end" and "lower end", as used herein, should be construed broadly to encompass portions of the sidewall of the tubular receptacle proximate the opposing longitudinal ends thereof. Accordingly, the present invention provides for a dual piston centrifuge tube that is effective for producing a more concentrated, purer and higher quality PRP. The apparatus may be employed analogously for separating other biological fluids into their constituent components and for aspirating the separated components from the fluid. The apparatus may be employed for a wide variety of surgical, medical and veterinary applications.

From the foregoing it may be seen that this invention provides for a method and system for more effectively and efficiently concentrating blood platelets for use in medical applications. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

What is claimed is:

1. A dual piston centrifuge tube assembly for separating and aspirating constituent components of a fluid biological product, said assembly comprising:
an elongate tubular receptacle having closed lower and upper ends;
a first common inlet and outlet port formed in one of said upper end and said receptacle which communicates with an interior chamber of said tubular receptacle, said first common inlet and outlet port adapted to introduce the fluid biological product into said chamber and to aspirate constituent components of the fluid biological product from said chamber;

a flexible, fluid-conducting pipe communicably connected to said first common inlet and outlet port and extending through said chamber of said tubular receptacle;

a first liquid impermeable piston mounted within said tubular receptacle and sealably engaging an interior surface of a longitudinal sidewall of said tubular receptacle for moving longitudinally through said chamber of said receptacle, said fluid-conducting pipe being disposed through said first piston such that a distal end of said pipe communicates with said receptacle chamber below said first piston;

a second liquid impermeable piston mounted within said tubular receptacle for longitudinally sliding through said chamber of said tubular receptacle between said first piston and said lower end of said receptacle, said second piston maintaining sealing interengagement with said interior sidewall of said tubular receptacle when said receptacle is centrifuged; and a second common inlet and outlet port formed by said lower end of said tubular receptacle and communicating with said chamber, said second common inlet and outlet port adapted to respectively introduce constituent components into and aspirate constituent components from said chamber;

the fluid biological product being introduced by said first common inlet and outlet port and said pipe into said interior chamber between said first and second pistons, said receptacle being centrifuged a first time to separate the fluid biological product into first and second constituent components, said first common inlet and outlet port for aspirating a first constituent component of the fluid biological product such that a suction is generated in said receptacle chamber and said first piston is drawn downwardly through said chamber to constrain the second constituent component in said chamber between said first and second pistons; the aspirated first constituent component being reintroduced into said chamber by said second common inlet and outlet port such that said first and second pistons and the constrained second constituent component are driven upwardly through said chamber and the first constituent component occupies said receptacle chamber between said second piston and said lower end of said receptacle; said receptacle being centrifuged a second time to separate the first constituent component into third and fourth constituent components constrained between said second piston and said lower end of said receptacle; said second common inlet and outlet having suction applied thereto to draw said second piston toward said lower end of said receptacle and aspirate at least one of the third and fourth constituent components from said chamber.

2. The assembly of claim 1 in which at least one of said first and second common inlet and outlet ports includes a respective self-sealing valve port.

3. The assembly of claim 1 in which said receptacle includes a capped upper end, which has a cap that is permanently and sealably fastened to said sidewall of said tubular receptacle.

4. The assembly of claim 3 in which said capped upper end carries a connective inlet element within said chamber of said tubular receptacle for communicably interengaging said first common inlet and outlet port and said fluid-conducting pipe.

5. The assembly of claim 1 in which said closed upper end includes a cap that is removably attached to said sidewall of said tubular receptacle.

6. The assembly of claim 1 in which said first and second pistons are sealably interengaged with said interior surface of said longitudinal sidewall of said tubular receptacle by respective sealing rings.

7. The assembly of claim 1 in which said second common inlet and outlet port includes a tubular stem that extends into said chamber of said tubular receptacle between said second piston and said lower end of said receptacle.

8. The assembly of claim 7 in which said second piston includes a receiving channel connected to a bottom surface of said second piston for receiving said tubular stem when said second piston moves toward said lower end of said tubular receptacle.

9. The assembly of claim 8 in which said bottom surface of said second piston and said lower end of said tubular receptacle are substantially coextensive and flat for flushly and conformably interengaging one another when said second piston slides to a lowermost position within said tubular receptacle.

10. The assembly of claim 1 in which said bottom surface of said second piston and said lower end of said tubular receptacle are substantially coextensive and flat for flushly and conformably interengaging one another when said second piston slides to a lowermost position within said tubular receptacle.

11. The assembly of claim 10 in which said second piston includes a substantially flat lower plate that is coextensive with said lower end of said receptacle such that when said second piston interengages said lower end of said receptacle, virtually all of the constituent components within said chamber between said second piston and said lower end of said receptacle are extracted and aspirated through said second common inlet and outlet port.

12. The assembly of claim 1 in which a vent is formed in said capped upper end of said tubular receptacle for equalizing air pressure within said tubular receptacle as fluid is added to or removed from said receptacle.

13. The assembly of claim 1 in which each of said first and second common inlet and outlet ports includes a respective luer port.

14. A method for separating fluid biological product into constituent components using a centrifuge tube assembly, which assembly includes an elongate tubular receptacle having a lower end and a capped upper end; a first, common inlet and outlet port formed in the capped upper end of the receptacle for communicating with an interior chamber of the tubular receptacle; a second common inlet and outlet port formed through the lower end of the tubular receptacle and communicating with the chamber; a flexible, fluid-conducting pipe communicably connected to the first common inlet and outlet port for extending through the chamber of the tubular receptacle; a first liquid impermeable piston mounted within the tubular receptacle and sealably engaging an interior surface of a longitudinal sidewall of the tubular receptacle for moving longitudinally through the chamber of said receptacle, a fluid-conducting pipe being disposed through the first piston such that a distal end of said pipe communicates with said receptacle chamber below the first piston; and a second liquid impermeable piston mounted within the tubular receptacle and sealably engaging the interior surface of the longitudinal sidewall of the tubular receptacle for longitudinally sliding through the chamber of the tubular receptacle between the first piston and the lower end of the receptacle, said method comprising:

introducing fluid biological product into the receptacle through the first common inlet and outlet port and fluid-conducting pipe below the first piston and above the second piston, such that the first piston is driven upwardly within said chamber as the fluid is introduced;

centrifuging the tubular receptacle a first time to separate the fluid into at least two constituent components;

aspirating a first constituent component from the receptacle chamber through the first common inlet and outlet port such that a suction is generated in the receptacle chamber, the first piston is drawn downwardly through the chamber of the tubular receptacle and a second constituent component is constrained in said chamber between the first and second pistons;

reintroducing the aspirated first constituent component into the chamber of the tubular receptacle through the second common inlet and outlet port such that the first and second pistons and the constrained second constituent component are driven upwardly through the tubular receptacle and the reintroduced first constituent component fills the tubular receptacle between the second piston and the lower end of the tubular receptacle;

centrifuging the tubular receptacle a second time to separate the first constituent components into third and forth constituent components constrained between said second piston and said lower end of the tubular receptacle; and sequentially aspirating the third and forth constituent components through the second common inlet and outlet port.

15. The method of claim 14 further including the steps of aspirating a first portion of the third constituent component through the second common inlet and outlet port such that a second portion of the third constituent component remains in the receptacle; agitating the receptacle to re-suspend at least some of the second portion of the third constituent component into the fourth constituent component; and aspirating the fourth constituent component from the tubular receptacle through the second common inlet and outlet port.

16. A method for separating blood product into constituent components using a centrifuge tube assembly, which assembly includes an elongate tubular receptacle having a lower end and a capped upper end; a first, common inlet and outlet port formed in the capped upper end of the receptacle for communicating with an interior chamber of the tubular receptacle; a second common inlet and outlet port formed through the lower end of the tubular receptacle and communicating with the chamber; a flexible, fluid-conducting pipe communicably connected to the first common inlet and outlet port for extending through the chamber of the tubular receptacle; a first liquid impermeable piston mounted within the tubular receptacle and sealably engaging an interior surface of a longitudinal sidewall of the tubular receptacle for moving longitudinally through the chamber of the receptacle, the fluid-conducting pipe being disposed through the first piston such that a distal end of the pipe communicates with the receptacle chamber below the first piston; and a second liquid impermeable piston mounted within the tubular receptacle and sealably engaging the interior surface of the longitudinal sidewall of the tubular receptacle for longitudinally sliding through the chamber of the tubular receptacle between the first piston and the lower end of the receptacle, the method comprising:

introducing blood product into the receptacle through the first common inlet and outlet port and fluid-conducting pipe below the first piston and above the second piston, such that the first piston is driven upwardly within the chamber as the blood product is introduced;

centrifuging the tubular receptacle a first time to separate the blood product into an upper layer including primarily a platelet/plasma suspension (PPS) and a lower layer including primarily red blood cells (RBC);

aspirating PPS from the receptacle chamber through the first common inlet and outlet port such that a suction is generated in the receptacle chamber, the first piston is drawn downwardly through the chamber of the tubular receptacle and the layer including primarily RBC is constrained in the chamber between the first and second pistons;

reintroducing the aspirated PPS into the chamber of the tubular receptacle through the second common inlet and outlet port such that the first and second pistons and the constrained layer of RBC are driven upwardly through the tubular receptacle and the reintroduced PPS fills the tubular receptacle between the second piston and the lower end of the tubular receptacle;

centrifuging the tubular receptacle a second time to separate the PPS into an upper layer of platelet poor plasma (PPP) and a lower layer of platelet rich buffy coat (PRB) between the second piston and the lower end of the tubular receptacle;

aspirating at least a portion of the upper layer of PPP through the second common inlet and outlet port;

re-suspending at least some of the platelets in the PPP layer into the PRB layer to produce platelet rich plasma (PRP); and aspirating the PRP from the tubular receptacle through the second common inlet and outlet port.

17. A dual piston centrifuge tube assembly for separating and aspirating constituent components of a fluid biological product, said assembly comprising:

an elongate tubular receptacle having a lower end and a capped upper end;

a first common inlet and outlet port formed in said capped upper end of said receptacle and communicating with an interior chamber of said tubular receptacle, said first common inlet and outlet port adapted to introduce the fluid biological product into said chamber and to aspirate constituent components of the fluid biological product from said chamber after said tube is centrifuged to separate the fluid biological product into first and second constituent components;

a flexible, fluid-conducting pipe communicably connected to said first common inlet and outlet port, which pipe extends through said chamber of said tubular receptacle;

a first liquid impermeable piston mounted within said tubular receptacle and sealably engaging an interior surface of a longitudinal sidewall of said tubular receptacle for moving longitudinally through said chamber of said receptacle, said fluid-conducting pipe being disposed through said first piston such that a distal end of said pipe communicates with said receptacle chamber below said first piston;

a second liquid impermeable piston mounted within said tubular receptacle and being longitudinally slidable through said chamber between said first piston and said lower end of said receptacle, said second piston maintaining sealing engagement with said interior surface of said longitudinal sidewall of said receptacle when said tube is centrifuged; and a second common inlet and outlet port formed through said lower end of said receptacle and communicating with said chamber, said second common inlet and outlet port adapted to respectively introduce the second constituent component of the fluid biological product into said chamber and aspirate at least one of a third constituent component and a fourth constituent component from said chamber after said receptacle is centrifuged to separate the second constituent component into the third and fourth constituent components; said second piston including a bottom surface that is configured such that when said second piston interengages said lower end, of said receptacle, virtually all constituent components in said chamber between said bottom surface of said second piston and said lower end of said receptacle are extracted and aspirated by said second common inlet, and outlet port.

18. The assembly of claim 17 in which said second common inlet and outlet port includes a tubular stem extending into said chamber of said receptacle between said second piston and said lower end of said receptacle, said second piston including a receiving channel connected to said bottom surface of said second piston for receiving said tubular stem when said second piston moves toward said lower end of said tubular receptacle, said bottom surface of said second piston and said lower end of said tubular receptacle being substantially coextensive and flat for flushly and conformably interengaging one another when said second piston slides into a lowermost position within said tubular receptacle.

19. The assembly of claim 17 in which said bottom surface of said second piston and said lower end of said tubular receptacle are substantially flat and coextensive for conformably and flushly interengaging one another when said second piston slides into a lowermost position with said tubular receptacle.

* * * * *

UNITED STATES PATENT AND TRADEMARK OFFICE
CERTIFICATE OF CORRECTION

PATENT NO. : 10,987,672 B2
APPLICATION NO. : 16/004053
DATED : April 27, 2021
INVENTOR(S) : Pennie Page 1 of 1

It is certified that error appears in the above-identified patent and that said Letters Patent is hereby corrected as shown below:

In the Claims

Claim 1, Column 13, Lines 20-21, Change "a second common inlet and outlet port formed by said lower end of said tubular receptacle" to --a second common inlet and outlet port formed through said lower end of said tubular receptacle--.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*